United States Patent [19]

Kennedy et al.

[11] Patent Number: 5,521,392

[45] Date of Patent: May 28, 1996

[54] LIGHT CURE SYSTEM WITH CLOSED LOOP CONTROL AND WORK PIECE RECORDING

[75] Inventors: John Kennedy, Guelph; Beverley Barber, Toronto, both of Canada; Gary Zubricky, West Seneca, N.Y.

[73] Assignee: EFOS Canada Inc., Mississauga

[21] Appl. No.: 235,621

[22] Filed: Apr. 29, 1994

[51] Int. Cl.$^6$ .............................. A61N 5/00; G21G 5/00
[52] U.S. Cl. .............................. 250/492.1; 250/504 R
[58] Field of Search ............................ 250/492.1, 504 R, 250/372, 372 EM

[56] References Cited

U.S. PATENT DOCUMENTS

| Re. 30,571 | 4/1981 | Bachur et al. | 315/151 |
|---|---|---|---|
| 3,614,682 | 10/1971 | Smith | 235/151.12 |
| 3,679,903 | 7/1972 | Blitchington | 250/83.3 UV |
| 3,705,787 | 12/1972 | Carli . | |
| 4,024,428 | 5/1977 | Bachur et al. | 315/151 |
| 4,032,817 | 6/1977 | Richmond | 315/149 |
| 4,033,263 | 7/1977 | Richmond | 101/416 A |
| 4,117,375 | 9/1978 | Bachur et al. | 315/151 |
| 4,396,872 | 8/1983 | Nutter | 315/308 |
| 4,399,100 | 8/1983 | Zsolnay | 422/62 |
| 4,417,179 | 11/1983 | Fujimura | 315/151 |
| 4,636,071 | 1/1987 | Lowe | 356/73.1 |
| 4,641,033 | 2/1987 | Petelin et al. | 250/504 R |
| 4,665,627 | 5/1987 | Wilde et al. | 250/372 |
| 4,716,097 | 12/1987 | Weed | 430/327 |
| 4,742,131 | 5/1988 | Asanuma | 526/61 |
| 4,819,177 | 4/1989 | Jurgensen | 364/476 |
| 4,819,842 | 4/1989 | Westervelt | 222/642 |
| 4,842,404 | 6/1989 | Duda | 356/218 |
| 4,930,504 | 6/1990 | Diamantopoulos | 128/395 |
| 5,137,800 | 8/1992 | Neckers | 430/281 |
| 5,139,331 | 8/1992 | Gentile | 356/218 |
| 5,395,591 | 3/1995 | Zimlich et al. | 250/372 |
| 5,418,369 | 5/1995 | Moore et al. | 250/492.1 |

OTHER PUBLICATIONS

Reprint from Adhesives Age, Apr. 1988—"UV Curing Cuts Time and Costs for Solenoid Manufacturer", by Michael Moreau; includes product brochure for Ultracure 100 on last page.

Reprint from Adhesive Age, Apr. 1990—"UV Spot Curing Is Safe and Has Space and Cost Benefits", by Beverley Barber; includes product brochure for Ultracure 100SS on last page.

Reprint from Adhesives Age, Apr. 1992, "UV Spot Cure Applications Enhance Electronic Processing", by John Beasley; includes product brochure for Ultracure 100SS on last page.

James Isaacson, "Medical Applications for UV Adhesives", presented Dec. 9–10, 1992.

*Primary Examiner*—Bruce C. Anderson
*Attorney, Agent, or Firm*—Bereskin & Parr

[57] ABSTRACT

An apparatus for producing a preselected amount of light energy for use with photosensitive materials. The apparatus comprises a source for producing light; a light guide for delivering the light produced by the source to a work site; (c) a sensor means for detecting the intensity of the light produced by the source; and (d) a controller for determining the amount of light energy to be delivered to the photosensitive material at the work site. The apparatus includes a dimmer for controlling the intensity of light delivered to the work site and a shutter for controlling the exposure time for the work site. The dimmer and shutter are controlled by the controller so that a predetermined total quantity of light energy is delivered to the work site.

25 Claims, 9 Drawing Sheets

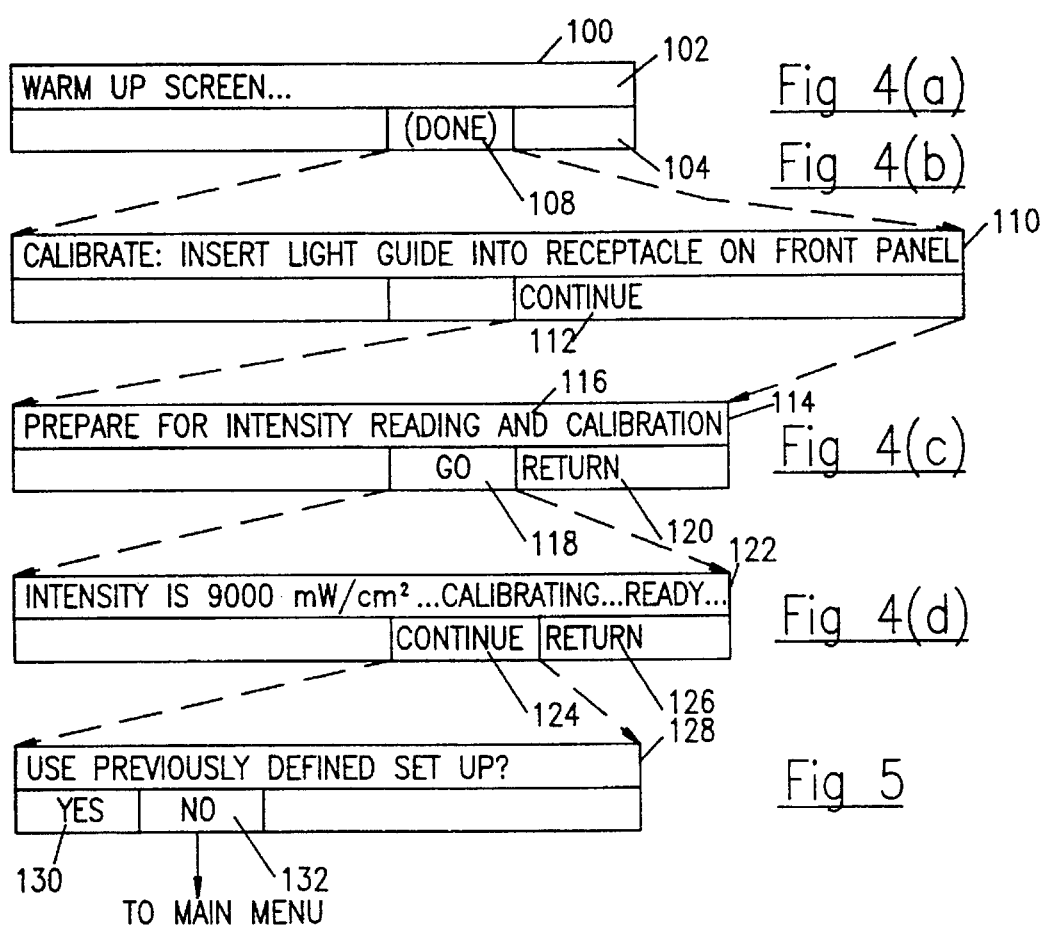

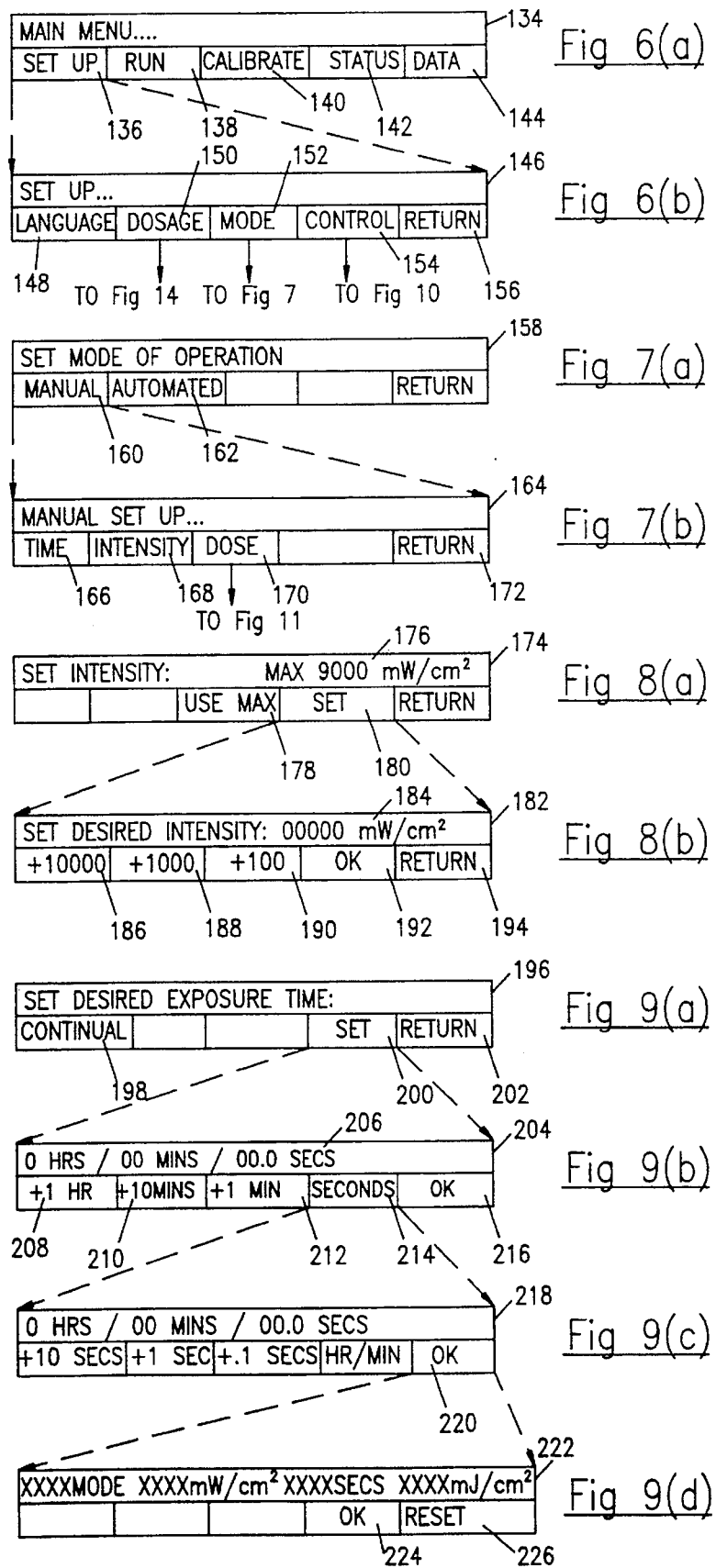

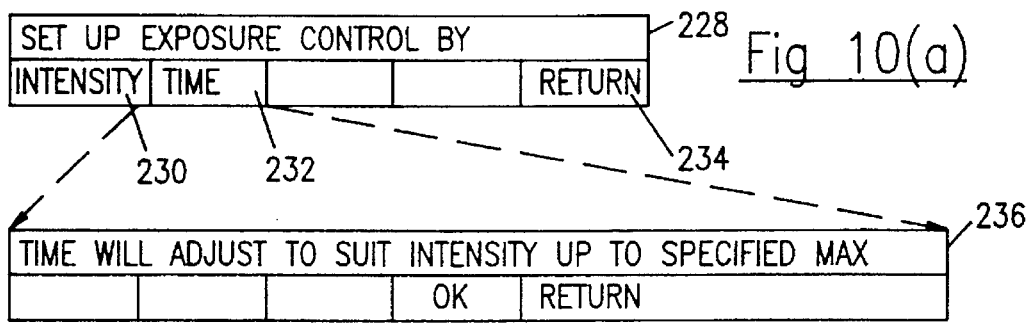
Fig 10(a)
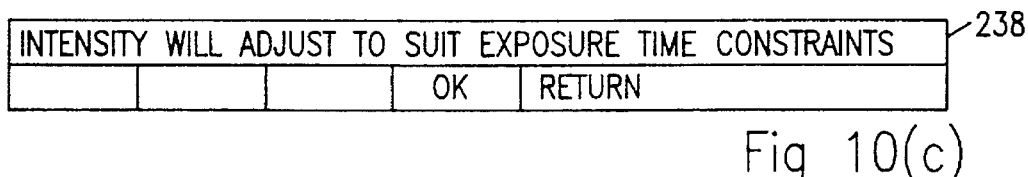
Fig 10(b)
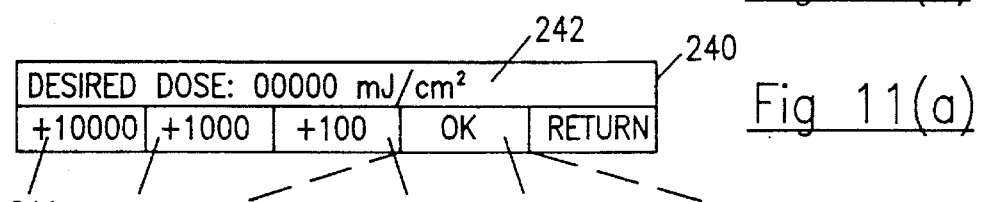
Fig 10(c)
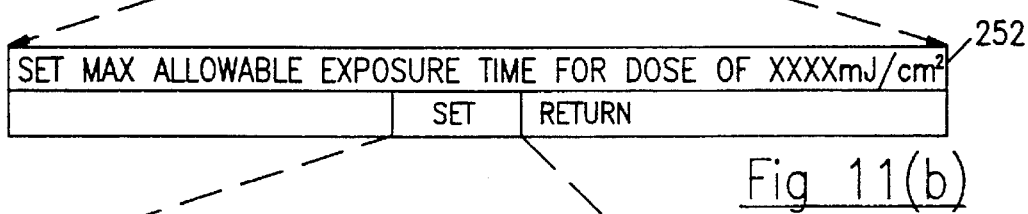
Fig 11(a)
Fig 11(b)
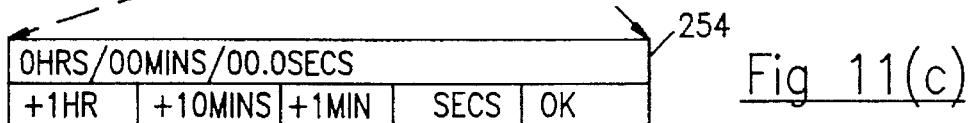
Fig 11(c)
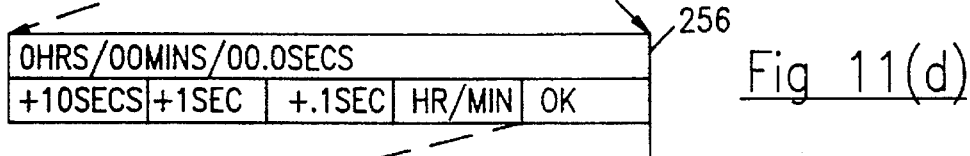
Fig 11(d)
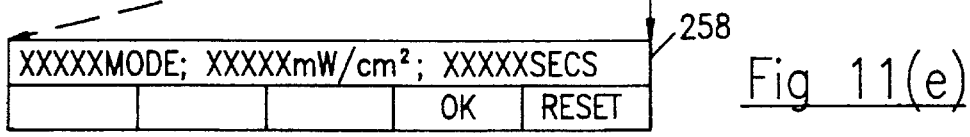
Fig 11(e)

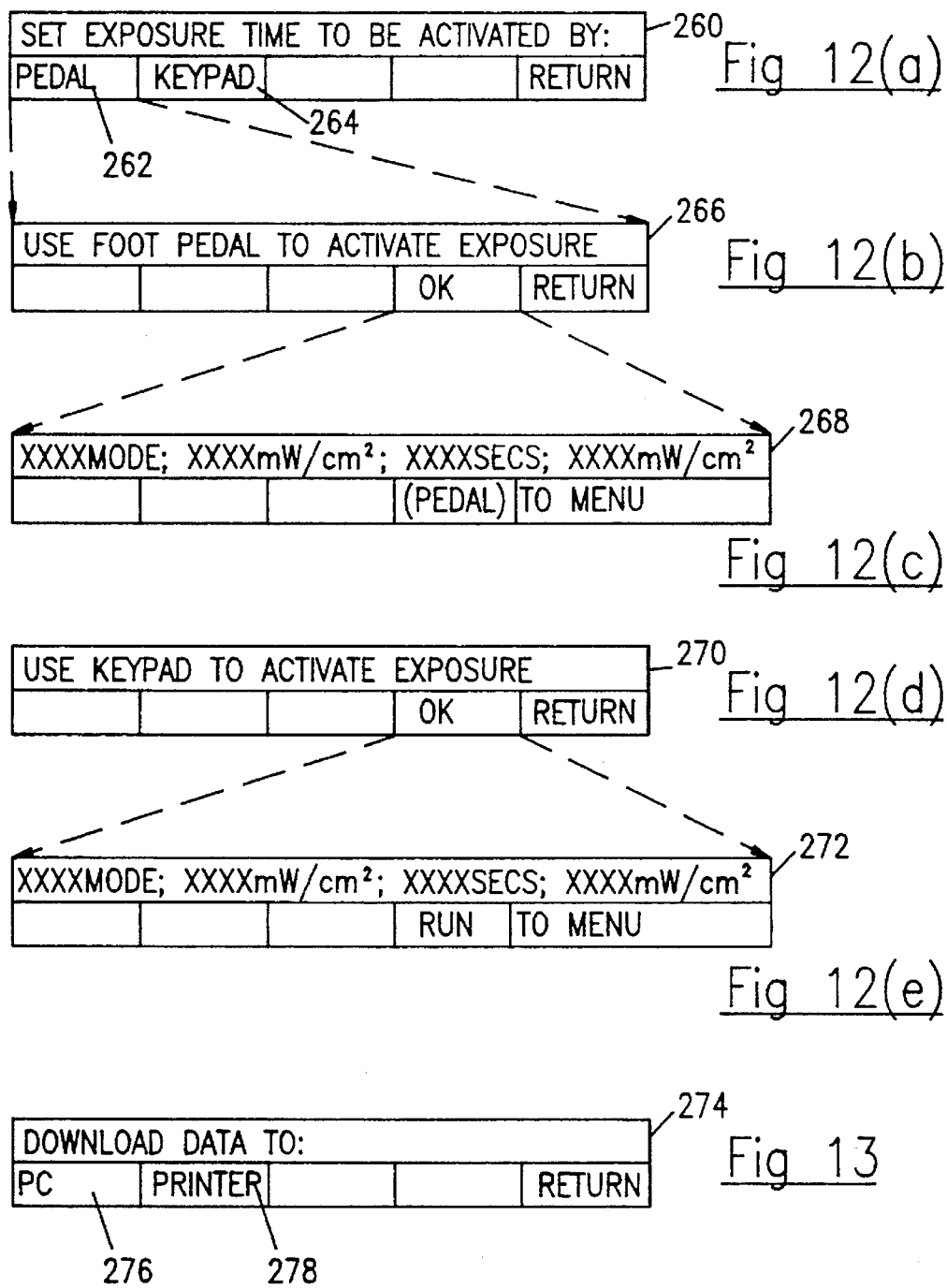

LIGHT CURE SYSTEM WITH CLOSED LOOP CONTROL AND WORK PIECE RECORDING

FIELD OF THE INVENTION

The present invention relates to a light cure system for photosensitive compounds. More particularly, it relates to a light cure system with closed loop control of the light energy delivered to a work piece and including data recording and work piece tracking.

BACKGROUND OF THE INVENTION

In the art, there are numerous substances which are sensitive to light energy. The substances of interest generally fall into two classes. The first class comprises substances which undergo polymerization in response to applied light energy. The second class comprise substances which produce a "singlet oxidation molecule" in response to applied light energy. The second class of substances can be found in "photodynamic therapy" or "phototherapy" applications, while the first class of photo-sensitive substances are typically found in UV polymerization and photochemical curing of adhesives.

It is known that the time it takes to cure a photosensitive adhesive is influenced by two principal factors. The first factor encompasses the type of adhesive and amount which is required for the application. Once determined for the particular application, this factor remains fixed for the application. The second factor affecting the cure time involves the amount of light energy being delivered to the cure the adhesive. It is also known that the intensity level produced by the light source will decrease over the life of the source. As the intensity level degrades so will the amount of light energy being delivered to cure the adhesive and therefore a longer exposure time is needed to properly cure the adhesive.

While known photochemical curing systems provide the capability to adjust the exposure time, they do not monitor the ongoing degradation of the intensity level produced by the light source. Thus, the performance of such a prior art system will steadily degrade over time unless the intensity level is manually measured and the exposure time adjusted accordingly.

Furthermore, in some applications, it may be desirable to increase the intensity level instead of the exposure time in order to provide an light energy output which is optimum for the curing application. Moreover, the light energy output level should be maintained at a consistent level over the operable life of the light source.

BRIEF SUMMARY OF THE INVENTION

In a first aspect the present invention provides an apparatus for producing a preselected amount of light energy for use with photosensitive materials, said apparatus comprising: (a) a source for producing light; (b) means for delivering the light produced by said source to a work site; (c) sensing means for detecting the intensity of the light produced by said source; and (d) a controller having means for determining a preselected amount of light energy for said work site and including light control means responsive to the detected intensity of the light produced by said source for controlling the amount of light delivered to said work site so that the preselected amount of light energy is delivered to said work site.

The system according to the present invention provides continuous intensity monitoring. The system also features the capability to adjust the exposure time or intensity level or both to compensate for output degradation in the light source and thereby provide a constant light energy output. The system also includes the capability to map the life of the light source and record or log system Usage, and also to track work pieces and exposure cycles.

BRIEF DESCRIPTION OF THE DRAWINGS

For a better understanding of the present invention, and to show more clearly how it may be carried into effect, reference will now be made, by way of example, to the accompanying drawings which show preferred embodiments of the present invention, and in which:

FIGS. 4(a) to 4(d) show the "Warm Up" and "calibration" screens for the user interface provided by the system of FIG. 1;

FIG. 5 shows the "Previous Set Up Selection" screen which is provided by the system of FIG. 1;

FIGS. 6(a) and 6(b) show the "Main Menu" and "Set Up" screens comprising the user interface;

FIGS. 7(a) and 7(b) show the "Set Mode" and "Manual Set Up" screens comprising the user interface;

FIGS. 8(a) and 8(b) show the screen sequence produced by the system of FIG. 1 for setting the intensity level;

FIGS. 9(a) to 9(d) show the screen sequence produced by the system for setting the exposure time;

FIGS. 10(a) to 10(c) show the screen sequence produced by the system for selecting the adjustment mode;

FIGS. 11(a) to 11(e) show the screen sequence produced by the system for entering a light dosage value for the system according to the present invention;

FIGS. 12(a) to 12(e) show the screen sequence produced by the system for selecting manual control of the shutter;

FIG. 13 shows the "Download Data" screen produced by the system of FIG. 1;

DETAILED DESCRIPTION OF THE PREFERRED EMBODIMENTS

Figure 1:
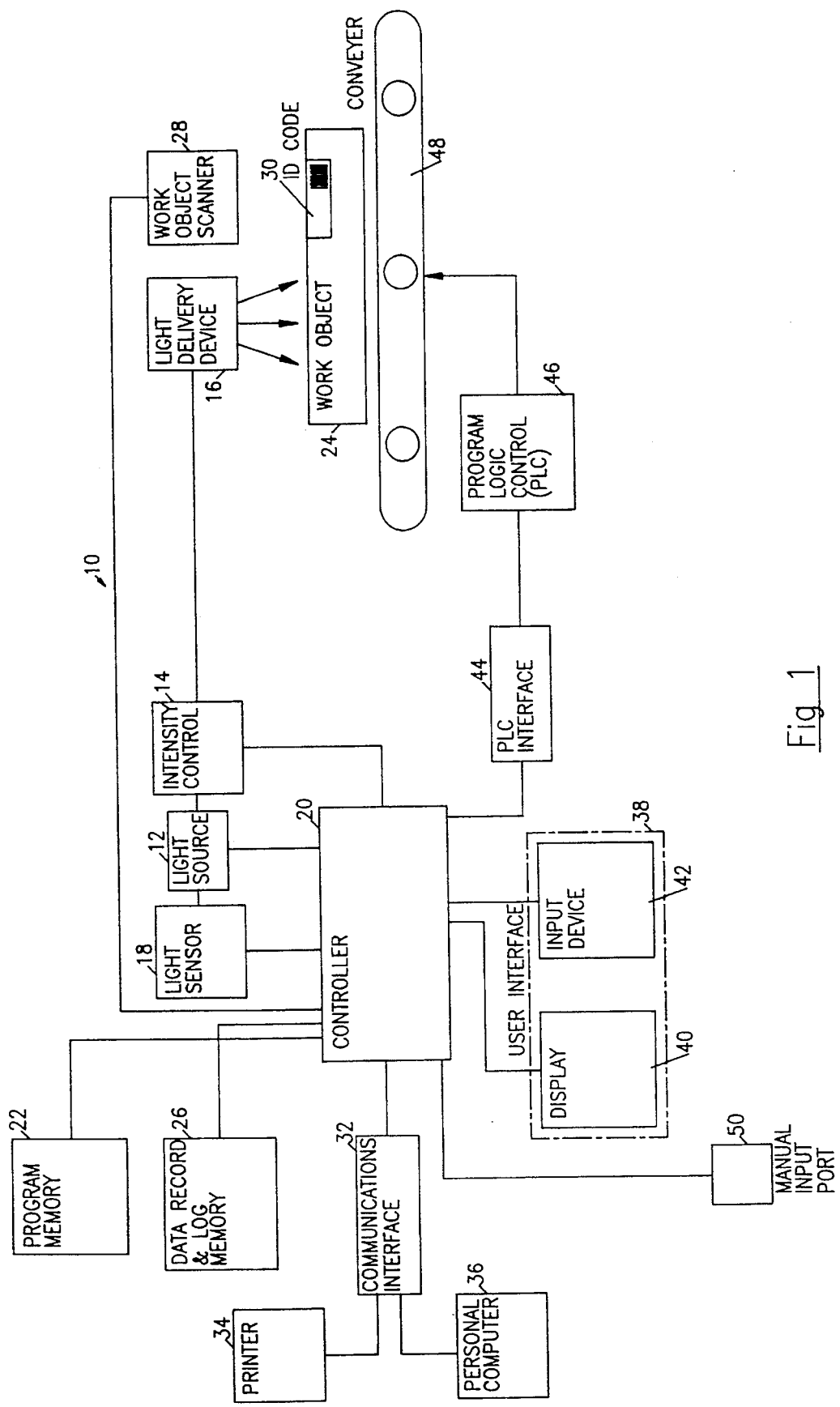
FIG. 1 is a block diagram showing a spot cure system according to the present invention.

Reference is first made to FIG. 1 which shows in block diagram form a system 10 according to the present invention. In the following description, the system 10 is described in the context of spot cure system for use curing photosensitive adhesives. However, the system 10 according to the invention is suitable for other applications involving photo-sensitive substances which require a pre-determined amount of light energy to cause a reaction, e.g. photodynamic therapy or phototherapy.

The spot cure system 10 comprises a light source 12, an intensity level and exposure time control module 14, a light source delivery device 16, and a light sensor 18. A controller 20 oversees and controls the operation of the system 10. The controller 20 executes a program (e.g. firmware) which is stored in program memory 22. Under the control of the controller 20, the light source 12 produces light energy which is delivered by the light delivery device 14 to a work piece 24.

The spot cure system 10 according to the invention provides a pre-determined amount of light energy to the work piece or object 24. The work piece 24 includes a photochemical substance which is sensitive and reacts to the applied light energy. The reaction is controlled by the amount of the light energy which is applied. The controller 20 controls the amount of light energy applied to the work piece 24 according to pre-selected parameters which have been inputted by a user or by an automated system. According to the invention, a consistent energy level is maintained by adjusting the exposure time and/or the intensity level to compensate for output degradation in the light source 12. As will be described in more detail below, the user can enter the desired energy level to be produced for the work object 24 and select which parameter is to be adjusted, i.e. intensity level or exposure time.

The controller 20 also includes memory 26 (e.g. RAM) which is used to store data records and other information associated with the operation of the system 10, for example, number of exposures, average exposure time, average daily run of the system 10, and a map of bulb life (intensity vs. time). To provide the additional capability to track the work pieces 24 and also correlate exposure information with the particular work piece 24, the system 10 can include a scanner 28, e.g. a bar-code scanner, which scans or reads a bar-code identifier 30 located on the work piece 24 as shown in FIG. 1. The bar code scanner 28 couples to the controller 20 in known manner. When the scanner 28 detects the bar code identifier 30, an ASCII character string is produced and fed to the controller 20. The controller 20 can then generate a data record for the work piece 24 using the ASCII code as an index and comprising the exposure information, e.g. intensity level, exposure time.

The data records are stored in memory 26 and can be downloaded through a communications interface 32. The communication interface 32 can comprise a conventional serial port, e.g. RS-232 interface, which connects the controller 20 to an external printer 34 or a personal computer 36.

The system 10 includes a user interface 38 comprising a display device 40 (e.g. a Liquid Crystal Display or LCD) and an input device 42 (e.g. keypad). In the preferred embodiment of the invention, the display 40 comprises a 2-line by 40-character LCD which is coupled to the controller 20 in known manner. The input device 42 comprises a five key pad which is mapped to the bottom line of the display 40 as "soft" keys. As will be understood by those skilled in the art, "soft" keys are context-dependent and can be integrated into a "user friendly" interface. The user interface 38 according to the present invention is described in more detail below with reference to FIGS. 5 to 14.

As shown in FIG. 1, the system 10 also includes a PLC (Programmable Logic Control) interface 44 which allows the system 10 to be operated in a semi-automated or automated mode. In known manner, the PLC interface 44 couples the controller 20 to a program logic control 46 which in turn is programmed to control a conveyor 48. The conveyor 48 carries work pieces 24 from station to station in an assembly line, for example, and one of the stations comprises the system 10. The system 10 can be operate in an automated mode under the control of the PLC 46. The PLC 46 controls operation of the system 10 by issuing commands and status requests to the controller 20 through the PLC interface 44. The nature of the interface and command interface between the PLC 46 and controller 20 is dependent on the operational parameters of the automated assembly line and will be within the understanding of one skilled in the art. For example, the maximum exposure time or dwell time, minimum intensity level and energy dosage can be downloaded by the PLC 46 and the controller 20 will issue a dwell time update command when the exposure time is increased.

The system 10 according to the invention can also be operated in a manual mode. In this mode of operation, the system 10 is configured by a user to run as a "stand-alone" system, i.e. without the PLC 46. In manual mode, each exposure cycle (i.e. curing cycle) is initiated by an external signal which is received by the controller 20 on a manual mode input port 50. The external signal can comprise an electronic signal which is generated by a switch activated by the operator.

Figure 2:
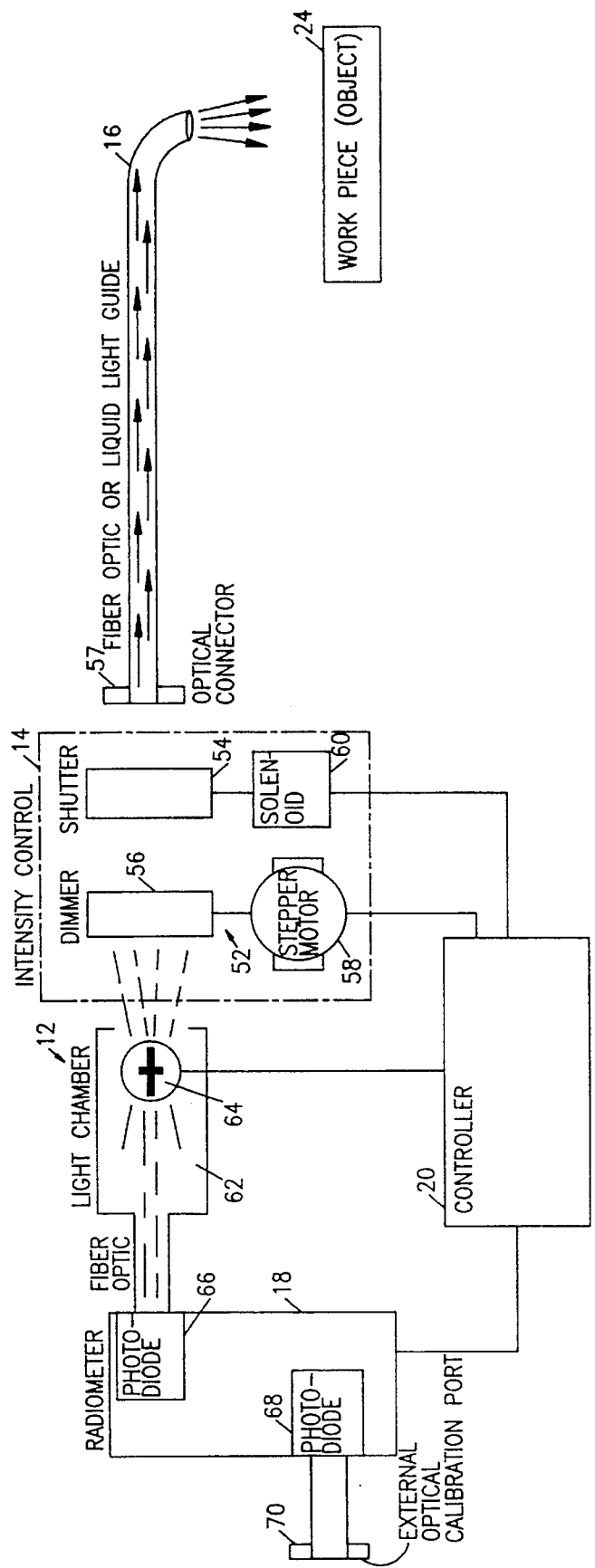
FIG. 2 is a block diagram showing in more detail the light delivery and sensing aspect of the system shown in FIG. 1.

Reference is next made to FIG. 2 which shows in more detail the intensity monitoring and control portions of the system 10 according to the invention. Like reference numbers in FIGS. 1 to 3 refer to like elements.

As shown in FIG. 2, the intensity control module 12 comprises a dimmer assembly 52 and a shutter 54. The dimmer assembly 52 comprises an adjustable dimmer 56 which is coupled to an output port the controller 20 through an actuator, for example, a stepper motor 58 as will be within the understanding of one skilled in the art. The shutter 54 is also coupled to an output port on the controller 20 through an actuator, for example a solenoid 60. As will be described in more detail below, the controller 20 uses the dimmer assembly 52 to control the intensity level of the light delivered to the work piece 24 and the shutter 54 to control the time the work object 24 is exposed by the light emitted by the source 12 through the dimmer 56. The light output from the shutter 54 and dimmer 56 are coupled to the light delivery device 16 through an optical connector 57. The optical connector 57 is selected according to the type of light delivery device 16. In most applications, the light delivery device 16 comprises a fiber optic cable or a liquid light guide. By using a flexible fiber optic cable or liquid light guide, the delivery device 16 can be maneuvered around the work piece 24, either manually or by machine, e.g. a robotic arm. In applications where it is not necessary to deliver a focused or collimated beam of the light, the fiber optic cable or liquid light guide can be eliminated, for example, where the light source 12 comprises a LED array which illuminates an area.

As is also shown in FIG. 2, the light source 12 comprises a light chamber 62 which houses a light bulb 64. The light bulb 64 can comprise known devices such as an arc source (e.g. mercury, xenon, or mercury/xenon), an incandescent source (e.g. quartz halogen), an "electrode-less" source (e.g. microwave source), or a solid state light source, e.g. a single light emitting diode (LED) or a multiple array device. The type of light bulb 64 which is selected depends on the characteristics of the photo-reactive substance on the work object 24, e.g. wavelength of the bulb 64, and the operational parameters for the system 10, e.g. maximum intensity level. The light chamber 62 couples the bulb 64 to the intensity control module 12 (i.e. dimmer 56 and shutter 54) and also to the light sensor module 18.

The light sensor module 18 in the preferred embodiment comprises a radiometer. As will be understood by one skilled in the art, the radiometer is a precision light measuring instrument. The radiometer 18 as shown in FIG. 2 is coupled to the controller 20 and includes two photodiodes 66 and 63. The first photodiode 66 is optically coupled to the light chamber 62. The controller 20 uses the output from the first photodiode 66 to monitor the intensity level of the light output from the bulb 64. The second photodiode 68 is optically coupled to an external calibration port 70. The calibration port 70 is used to measure the light delivered to the work object 24 at the emitting end of the fiber optic cable or liquid light-guide 16. The controller 20 can use the light measured by the second photodiode 68 and the first photodiode 66 to detect degradation in the light delivery capability of the fiber optic cable or light guide 16.

As the bulb 64 ages, the intensity level of the light output will tend to decrease. To maintain the optimum light energy delivered to the work object 24, the controller 20 measures the current intensity level of the bulb 64. If the desired light energy amount cannot be maintained by the current intensity level, the controller 24 will make an adjustment in the intensity level output by opening the dimmer 56). The controller 20 can also compensate for the degradation of the bulb 24 by increasing the exposure time by opening the shutter 54 for a longer time. Both of these adjustment modes are described below with reference to FIG. 10. The operator selects the adjustment mode, i.e. exposure time adjustment or intensity adjustment as will also be described below with reference to FIGS. 10(a) to 10(c).

Figure 3:
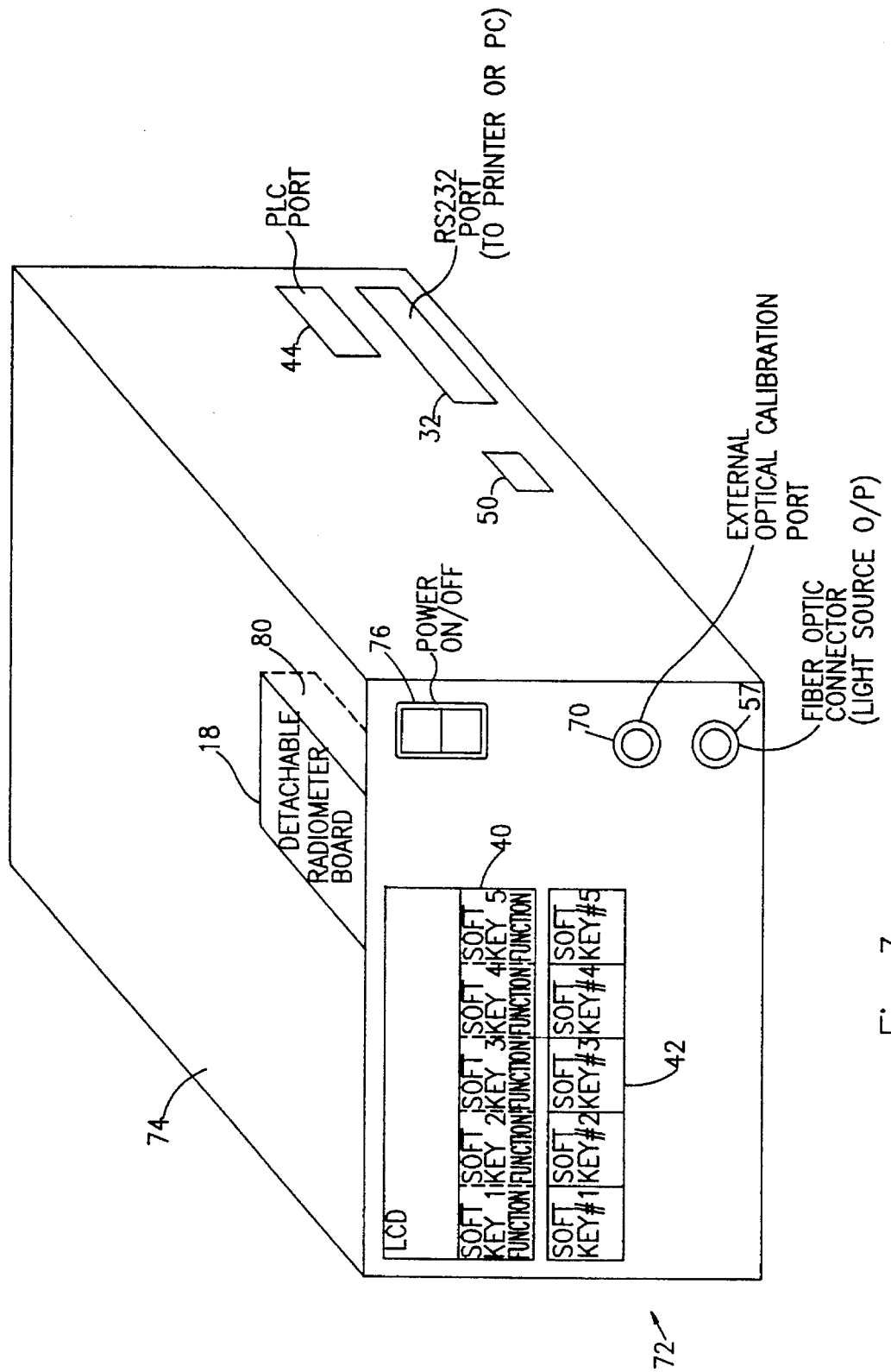
FIG. 3 is a diagram showing the system of FIG. 1 implemented as a work station.
Figures 14A, 14B, 14C, 14D, 14E, 14F, 14G, 14H, 14I, 14J, 14K:
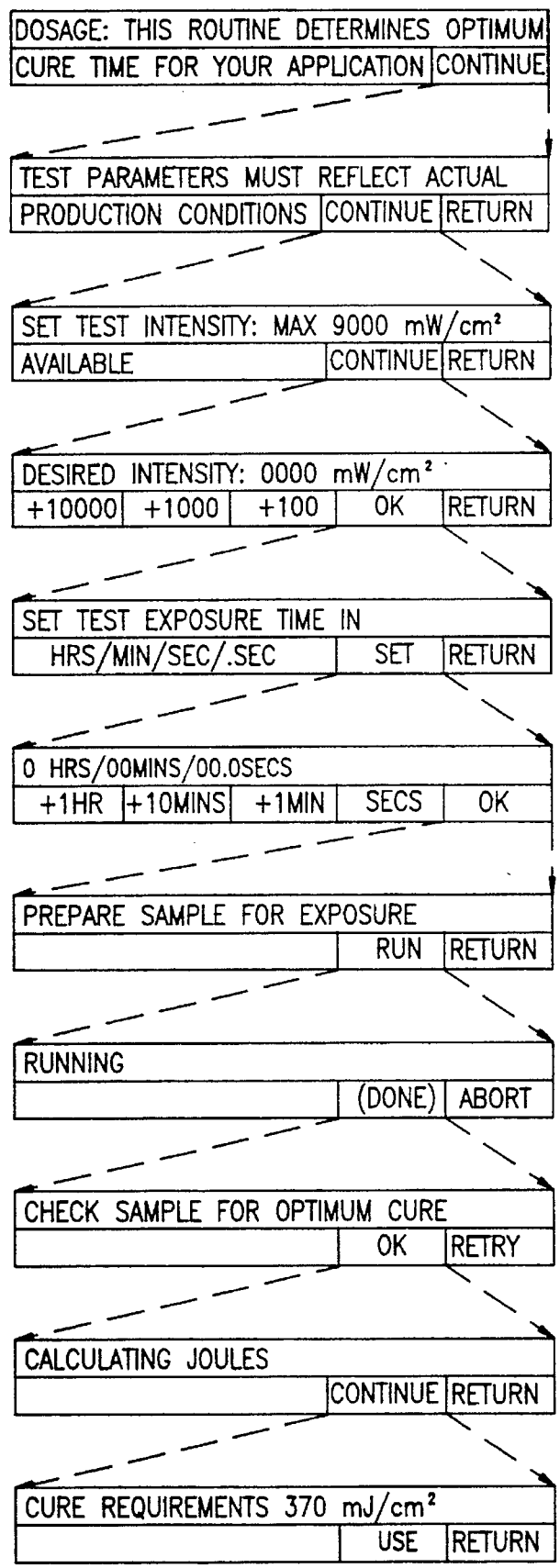
FIGS. 14(a) to 14(k) shows the screen sequence produced by the system for an on-line routine to determine application specific dosage requirements.

Reference is next made to FIG. 3 which shows in diagrammatic form an implementation of the system 10 of FIG. 1 as an integrated work station 72. The work station 72 comprises a cabinet 74 which houses the components of the system 10. As shown in FIG. 3, the display 40 and key pad 42 are mounted on the front panel of the cabinet 74. The front panel of the cabinet 74 includes the fiber optic connector port 57 and the external calibration port 70. The front panel of the a cabinet also includes a power on/off switch 76. As shown in FIG. 3, the cabinet 74 also includes appropriate connectors for the communication interface 32 and the PLC interface 44.

Referring still to FIG. 3, the radiometer 18 is packaged as a detachable module 80. The detachable design allows the radiometer 80 to be easily removed for calibration. Since it is desirable to calibrate the radiometer 80 according to industry standards, e.g. NIST (National Institute of Standards Technology) parameters, calibration will typically be off-site and thus it is convenient and useful to remove the module 80 for testing and plug a spare radiometer (not shown) which has been calibrated.

Reference is next made to FIG. 4(a) which shows a "Warm Up" screen 100 which is produced by the controller 20 when the system 10 is being initialized, e.g. when the power if first turned on.

As shown in FIGS. 4 to 14, the screens produced by the system 10 according to the invention comprise a first line 102 and a second line 104, which correspond to the two lines on the LCD 40 (FIGS. 1 and 3). The first line 102 is reserved for prompt messages or status messages. The second line 104, on the other hand, is used to display the soft key functions which have been assigned to the corresponding soft keys in the key pad 42. According to the invention, the functions of the keys in the pad 42 change depending on the screen, i.e. context, and the function associated with a softkey is displayed on the second line in a portion above the key. Pressing a key causes the controller 20 to execute the function currently associated with that key in the screen. In some screens not all five soft keys will be assigned and therefore, a portion of the second line 104 can be made available to display a prompt message which overflows the first line 102, e.g. more than 40 characters.

Referring to FIG. 4(a), when the system 10 is first turned on (or in response to a reset), the controller 20 executes an initialization routine. The initialization routine involves initializing the peripherals coupled to the controller 10, e.g. the display 40, communications interface 32 and the PLC interface 44, performing a "RAM" or memory check and other self diagnostics. In addition, the controller 20 sets the dimmer 56 to a default position of wide open, i.e. maximum intensity. Once the controller 10 has completed the initialization routine, a DONE softkey 108 is activated on the display 40 and key pad 42.

In response to the user pressing the DONE key 108, the controller 20 displays a "Calibrate" prompt screen 110 which comprises a CONTINUE softkey 112 as shown in FIG. 4(b). According to the invention, the system 10 must obtain an intensity reading from the end of the fiber optic cable or liquid light guide 16 before it will proceed further. The controller 20 displays another screen 114 when the CONTINUE softkey 112 is pressed. As shown in FIG. 4(c), the screen 114 comprises a prompt 116 on the top line 102 and two softkeys GO 118 and RETURN 120. The prompt 116 notifies the user to insert the emitting end of the fiber optic cable 16 into the calibration port 70 (FIGS. 1 and 3) and then press the GO key 118. The controller 20 then determines the intensity level (via the photodiode 68 in the radiometer 18) and the measured intensity level is displayed on the top line of another screen 122 as shown in FIG. 4(d). The screen 112 includes a CONTINUE softkey 124 and a RETURN softkey 126. Pressing the RETURN key 126, returns the user to the CALIBRATE screen 110.

Referring still to FIG. 4(d), if the user presses the CONTINUE key 126, the controller 20 checks if a previous set up has been entered. If yes, the controller 20 displays a screen 128 as shown in FIG. 5. The screen 128 includes a prompt on the top line as shown and two softkeys YES 130 and NO 132. If YES 130 is pressed, the controller 20 retrieves the previously stored set up. If NO 132 is pressed, the controller 20 displays a "MAIN MENU" screen 134 as shown in FIG. 6(a).

Referring to FIG. 6(a), the Main Menu screen 134 includes a SETUP softkey 136, a RUN softkey 138, a CALIBRATE softkey 140, a STATUS softkey 142 and a DATA softkey 144.

The RUN key 138 is used to control the "manual" mode of operation and is described in more detail below with reference to FIGS. 12(a) to 12(e). The CALIBRATE key 140 allows the user to initiate a calibration and the controller 20 produces a sequence of screens as shown in FIGS. 4(b) to 4(d) described above. The STATUS key 142 produces a status screen which displays the current intensity level, exposure time, the lamp hours, the energy level, and the mode, i.e. manual or automated. The DATA key 144 is used to access a PC/Printer download screen which is described in more detail with reference to FIG. 13.

If the SET UP key 136 is pressed, the controller 20 displays a SET UP sub-menu screen 146 as shown in FIG. 6(b). The sub-menu screen 146 includes another five softkeys which provide the user with various set up functions. The softkeys comprise a LANGUAGE softkey 148, a DOSAGE softkey 150, a MODE softkey 152, a CONTROL softkey 154 and a RETURN softkey 156.

Pressing the LANGUAGE key 154 causes the controller 20 to display a screen (not shown) which allows the user to select the Language, e.g. English, French, German or Spanish.

The DOSAGE softkey 150 is used by the operator to access an on-line routine which helps the operator determine the dosage for a specific application. The operation of the DOSAGE softkey 150 is described in more detail below with reference to FIGS. 14(a) to (k).

The MODE softkey 152 allows the user to select the "Manual" or "Automated" mode of operation. In the Manual mode, a curing or light cycle is initiated by an external signal source, such as a foot pedal coupled to the manual input port 50, or a user entry on the key pad 42. In the Automated mode, a curing or light cycle is initiated by another external signal source, for example, the output from the PLC 46. It will be appreciated that in both Manual and Automated modes, the curing cycle is initiated by an external signal, and the difference lies in the source of the external signal and the degree of the control exercised e.g. full external control in automated mode.

The CONTROL softkey 154 allows the user to select the parameter which will be adjusted in order to maintain the predetermined energy level which is delivered to the work piece 24. According to the invention, the controller 20 can maintain a constant energy level by varying the exposure time or by varying the intensity level. The controller 20 uses the shutter 54 to control the exposure time, e.g. exposure time is increased by opening the shutter 54 for a longer period. To control the intensity level, the controller 20 operates the dimmer 56. For example, if the output from the bulb 64 has decreased, the controller 20 can increase the intensity level by further opening the dimmer 56. It will be appreciated by those skilled in the art that there are certain photo-reactive applications where a lower intensity over a longer period is useful and preferable to high intensity over a shorter period. For example, exposure to low intensity light over a longer period can produce longer molecule bonding chains in certain photo-sensitive substances, and in the manufacture of certain types of contact lenses, low intensity light is needed to prevent shrinkage and warping. The operation of the CONTROL softkey 154 is described in more detail with reference to FIGS. 10(a) to 10(c).

Referring still to FIG. 6(b), pressing the RETURN key 156 causes the controller 20 return to the Main Menu screen 134 shown in FIG. 6(a).

The operation and set up of the system 10 in manual mode will now be described with reference to FIGS. 7 to 11. Pressing the MODE key 152 in the Set Up screen 146 causes the controller 20 to display a screen 158 as shown in FIG. 7(a). The screen 158 comprises a prompt 160 on the top line and two softkeys MANUAL 160 and AUTOMATED 162. Pressing the MANUAL key 160 causes the controller to display a Manual Set Up screen 164 as shown in FIG. 7(b).

Referring to FIG. 7(b), the Manual Set Up screen 164 comprises four softkeys: TIME 166, INTENSITY 168, DOSE 170 and RETURN 172. The operator uses the TIME 166 key to enter the exposure time for the curing application, and the INTENSITY key 168 to enter the intensity level. The DOSE key 170 is for entering the amount of energy (in milliJoules) which is required for the curing cycle.

Pressing the INTENSITY key 168 causes the controller 20 to display a Set Intensity screen 174 as shown in FIG. 8(a). The screen 174 comprises a prompt 176 on the top line and two softkeys: USE MAX 178 and SET 180. The prompt 176 displays the current intensity level measured by the radiometer 18 and controller 20, and corresponds to the maximum intensity available, i.e. the dimmer 56 is wide open. To use the maximum intensity level, the user presses the USE MAX key 178. To enter a value for the intensity level, the user presses the SET key 180. In response, the controller 20 displays a Set Desired Intensity screen 182 as shown in FIG. 8(b).

Referring to FIG. 8(b), the Set Desired Intensity screen 182 comprises a prompt 184 and five softkeys: +10000 key 186, +1000 key 188, +100 key 190, an OK key 192 and a RETURN key 194. The prompt 184 displays the current intensity level which has been entered by the user through the softkeys 186 to 190. When the desired intensity level has been entered, the user pushes the OK key 192 to save the intensity setting. The controller 20 then uses the intensity setting to determine the amount the dimmer 56 should be opened (or closed). Pressing the RETURN key 194 causes the controller 20 to return to the previous screen without saving the user entered intensity level.

Referring back to FIG. 7(b), pressing the TIME key 166 causes the controller 20 to display a Set Exposure Time screen 196 as shown in FIG. 9(a). The screen 196 comprises a prompt on the top line and a CONTINUAL softkey 198, a SET softkey 200 and a RETURN softkey 202. Pressing the CONTINUAL key 198 causes the controller 20 to set the shutter 54 open. If the user presses the SET key 200, the controller 20 displays an Exposure Time Input screen 204 as shown in FIG. 9(b).

Referring to FIG. 9(b), the Exposure Time Input screen 204 comprises a prompt 206 and five softkeys: +1 Hr key 208, +10 Mins key 210, +1 Min key 212, a SECONDS key 214 and an OK key 216. The operator uses the three keys 208,210,212 to enter the exposure time which is displayed as the prompt 206. If the user wishes to enter the "seconds" portion for the exposure time, the user presses the SECONDS key 214 which causes the controller 20 to display an input screen 218 as shown in FIG. 9(c). To save the exposure time entry, the screen 218 includes an OK key 220. Pressing the OK key 220 causes the controller 20 to save the time entered by user and vary the operating parameters for the shutter 56 accordingly. In addition, the controller 20 displays a screen 222 as shown in FIG. 9(d). The screen 222 shows the current settings (on the top line) which have been entered and provides an OK softkey 224 for verifying the settings or a RESET key 226 for clearing the settings.

Referring back to FIG. 7(b), pressing the DOSE key 170 causes the controller 20 to display a Dosage input screen 240 as shown in FIG. 11(a). The screen 240 comprises a prompt 242 which shows the desired dosage currently entered. The screen 240 also includes three softkeys: +10000 key 244, +1000 key 246, and +100 key 248 for entering the dosage value, and an OK softkey 250. Pressing the OK key 250 causes the controller 20 to display a screen 252 for setting the maximum allowable exposure time for the dosage value entered in the previous screen 240. The user enters the maximum exposure time using screens 254 and 256 as shown in FIGS. 11(c) and 11(d) respectively. The user verifies the entered dosage value and maximum exposure time using screen 258 shown in FIG. 11(e).

Once the manual set up parameters have been entered, the user presses the RETURN key 172 in the Set Up screen 164 to return to the Set Up screen 146. Referring back to the Set Up screen 164 in FIG. 6(b), the user can now select the mode for adjustment control. Pressing the CONTROL key 154 causes the controller 20 to display a screen 228 as shown in FIG. 10(a). The screen 228 shown in FIG. 10(a) comprises an INTENSITY softkey 230, a TIME softkey 232 and a RETURN softkey 234. Pressing the TIME key 232 causes the controller 20 to display a screen 236 as shown in FIG. 10(*b*) which allows the user select the time adjustment mode. In the time adjustment mode, the controller 20 increases the exposure time up to a pre-determined maximum value (via the shutter 56) as the output of the bulb 64 degrades. Pressing the INTENSITY key 230 causes the controller 20 to display a screen 238 as shown in FIG. 10(*c*). The screen 238 allows the user to select the intensity adjustment mode, i.e. the controller 20 increases the opening of the dimmer 54 to compensate for degradation in the bulb 64 and maintain a consistent energy output level to the work piece 24.

Once the user has completed entering the set up parameters, e.g. for manual mode as described above, the user can start the system 10 by pressing the RUN key 138 in the Main Menu 134 shown in FIG. 6(*a*). Pressing the RUN key 138 causes the controller 20 to display a screen 260 as shown in FIG. 12(*a*). The screen 260 allows the user to select the source of the manual input signal for initiating the curing cycle. As shown in FIG. 12(*a*), the screen 260 includes a softkey 262 for selecting a PEDAL input (coupled to the manual input port 50—FIG. 1) and a softkey 264 for selecting a key pad for the trigger input. Pressing the PEDAL key 262 causes the controller 20 to display a verification screen 266 as shown in FIG. 12(*b*) and verifying the manual input source causes the controller 20 to display a screen 268 as shown in FIG. 12(*c*). If the user selects the key pad 42 as the manual input, the controller 20 displays a screen 270 as shown in FIG. 12(*d*) and generates a screen 272 as shown in FIG. 12(*e*) when the user verifies the selection.

Referring back to FIG. 6(*a*), to download the logged data, the user presses the DATA key 144 in the Main Menu 134. Pressing the DATA key 144 causes the controller 20 to display a Download Control screen 274 as shown in FIG. 13. The Download Control screen 274 provides the user with a PC softkey 276 for downloading the data to another computer 36 (FIG. 1) or a PRINTER softkey 278 for "dumping" the data to the printer 34 coupled to the communications interface 32.

Reference is next made to FIGS. 14(*a*) to 14(*k*) which show the screen sequence produced by the system 10 for the on-line routine which is used to determine application specific dosage requirements. For example, there may be instances where the operator does not know the dosage for a particular type of adhesive or application. By following the prompts and steps in the screens as shown in FIGS. 14(*a*) to (*k*), the system 10 helps the operator determine the dosage for a particular application. The on-line routine shown in FIG. 14 is accessed by pressing the DOSAGE softkey 150 in the Set Up screen 146 shown in FIG. 6(*b*).

Figure 15:
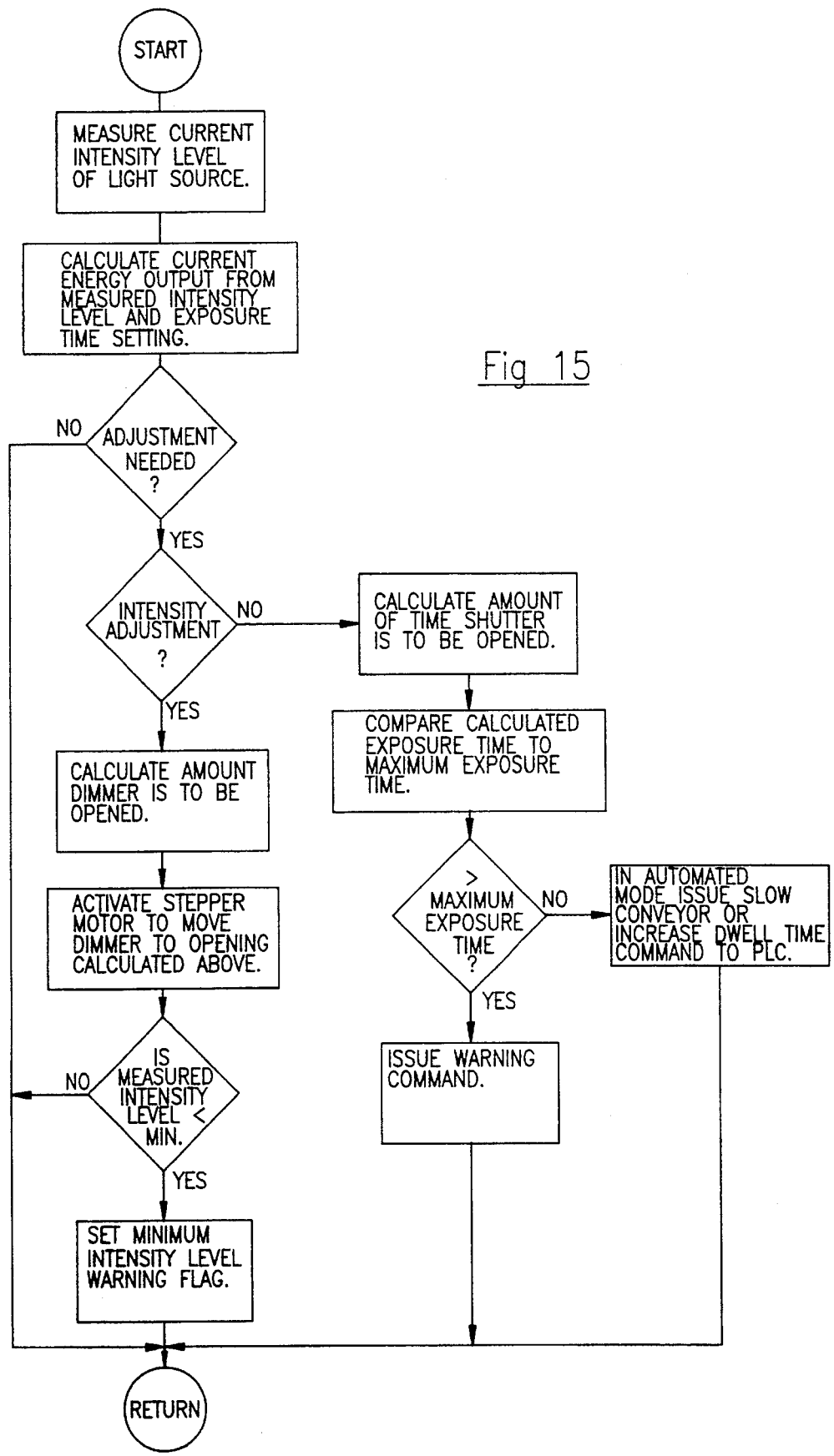
FIG. 15 is a logical flow diagram showing the method steps performed to monitor and adjust the light energy delivered by the system of FIG. 1.

Lastly reference is made to FIG. 15 which provides a logical flow diagram for the steps executed by the controller 20 to maintain a consistent energy output level according to the pre-determined set up and operating parameters (e.g. maximum exposure time and intensity adjustment mode) and the current intensity output level of the light source.

Although various preferred embodiments of the present invention have been described in detail, it will be appreciated by those skilled in the art, that variations may be made without departing from the spirit of the invention or the scope of the appended claims.

I claim:

1. An apparatus for producing a preselected amount of light energy for use with photosensitive material, said apparatus comprising:

(a) light production means for producing light;

(b) light delivery means for delivering the light produced by the light production means to a work site having curable photosensitive material;

(c) first sensing means for detecting the intensity of the light produced by the light production means and generating first signals correlated therewith;

(d) second sensing means for sensing the intensity of the light delivered by the light delivery means and generating second signals correlated therewith; and (e) control means responsive to the first signals and to the second signals for controlling the amount of light energy delivered to said work site, based upon preselected control parameters, and said control means comprising:

(i) storage means for storing said control parameters;

(ii) input means for inputting said first signals and said second signals;

(iii) timing means;

(iv) processing means for generating control signals based upon the first signals, the second signals, the timing means and the control parameters;

(v) output means for outputting the control signals to the light production means; and (vi) data storage means for storing data relating to the amount of light energy produced.

2. Apparatus as defined in claim 1, wherein the light production means comprises:

(a) a light source;

(b) intensity control means responsive to control signals for controlling the intensity of light produced by the light production means; and (c) exposure control means responsive to control signals for controlling an exposure time of light during which light is produced by the light production means.

3. Apparatus as defined in claim 2, wherein the intensity control means comprises a dimmer assembly.

4. Apparatus as defined in claim 3, wherein the exposure control means comprises a shutter.

5. Apparatus as defined in claim 2, wherein the processing means also determines over pre-selected periods of time the amount of light energy produced by the light production means, the number of exposures, average exposure time, and variation of the intensity of light produced by the light source over time and stores this information in said data storage means.

6. Apparatus as defined in claim 6, wherein the control means also comprises control data interface means for inputting control parameters and outputting data stored in the storage means and the data storage means.

7. Apparatus as defined in claim 6, wherein the control data interface means comprises a display device for displaying information to a user, and a data input device for the user to input control parameters.

8. Apparatus as defined in claim 6, wherein the control data interface means comprises a programmable logic control interface which inputs control parameters from a remote computer, and which outputs data stored in the storage means and in the data storage means, and data correlated with the first signals and the second signals to the remote computer.

9. Apparatus as defined in claim 2, wherein the processing means also determines over pre-selected periods of time one or more computations from the set including:

(a) the amount of light energy produced by the light production means;

(b) the number of exposures;

(c) average exposure time; and (d) variation of the intensity of light produced by the light source over time.

10. Apparatus as defined in claim 9, wherein the control means also comprises control data interface means for inputting control parameters and outputting data stored in the storage means and the data storage means.

11. Apparatus as defined in claim 10, wherein the control data interface means comprises a display device for displaying information to a user, and a data input device for the user to input control parameters.

12. Apparatus as defined in claim 10, wherein the control data interface means comprises a programmable logic control interface which inputs control parameters from a remote computer, and which outputs data stored in the storage means and in the data storage means, and data correlated with the first signals and the second signals to the remote computer.

13. Apparatus as defined in claim 1, wherein the light delivery means comprises a fiber optic cable.

14. Apparatus as defined in claim 1, wherein the light delivery means comprises a liquid light-guide.

15. Apparatus as defined in claim 1, wherein the second sensing means is located proximate the light delivery means.

16. Apparatus as defined in claim 1, wherein the second sensing means is located in an external calibration port.

17. Apparatus as defined in claim 1, wherein the first sensing means comprises a photodiode.

18. Apparatus as defined in claim 17, wherein the photodiode of the first sensing means is insertably removable.

19. Apparatus as defined in claim 1, wherein the second sensing means comprises a photodiode.

20. Apparatus as defined in claim 19, wherein the photodiode of the second sensing means is insertably removable.

21. A method of operating a light curing device which delivers light energy of curing wavelength to a work site for curing photosensitive material during an exposure, said device having a light source, a controller, light sealing means, light dimming means, and light sensing means, the method comprising the steps of:

(a) operating the light source;

(b) determining a desired total amount of curing light energy to be delivered to said work site during said exposure for curing photosensitive material at said work site;

(c) opening said light sealing means to commence said exposure;

(d) continuously monitoring the intensity of light energy emitted through said light dimming means;

(e) continuously summing the total light energy emitted through said light dimming means during said exposure; and (f) controlling said light dimming means and said light sealing means so that said desired total amount of light energy is delivered to said work site during said exposure.

22. The method defined in claim 21 further comprising the step of determining one or more desired operational parameters from the set including:

(a) maximum exposure time;

(b) minimum intensity level of light energy to be delivered to said work site during said exposure;

(c) maximum intensity level of light energy-to be delivered to said work site during said exposure; and (d) desired intensity, level of light energy to be delivered to said work site during said exposure.

23. The method defined in claim 22 further comprising the step of storing data correlatable with said determined desired total amount of curing light energy, said determined operational parameters, said monitored intensity of light energy and said summed total light energy emitted.

24. The method defined in claim 23 further comprising the step of outputting said stored data to an interface means.

25. The method defined in claim 22 further comprising the step of generating a signal indicative thereof in the event that a determined parameter is breached.

* * * * *